United States Patent [19]

Kinnel

[11] Patent Number: 5,125,912
[45] Date of Patent: Jun. 30, 1992

[54] DEVICE FOR THE WITHDRAWAL OF NEEDLES

[76] Inventor: Marc Kinnel, 2 rue de la Fontaine, 57420 Coin Sur Seille, France

[21] Appl. No.: 591,689

[22] Filed: Oct. 3, 1990

[51] Int. Cl.⁵ .................. B61M 5/00; B65D 83/10
[52] U.S. Cl. ............................. 604/263; 206/365
[58] Field of Search .......... 604/110, 192, 195, 198, 604/263; 206/365, 366

[56] References Cited

U.S. PATENT DOCUMENTS

| | | | |
|---|---|---|---|
| 2,962,155 | 11/1960 | Rusciano | 206/365 |
| 4,938,514 | 7/1990 | D'Addezio | 604/192 |
| 4,955,865 | 9/1990 | Steiner et al. | 604/263 |
| 4,981,476 | 1/1991 | Alchlamyr et al. | 604/192 |

FOREIGN PATENT DOCUMENTS

| | | | |
|---|---|---|---|
| 2205043 | 11/1988 | United Kingdom | 604/263 |
| 2215215 | 9/1989 | United Kingdom | 604/263 |

Primary Examiner—C. Fred Rosenbaum
Assistant Examiner—Sharon Finkel
Attorney, Agent, or Firm—Weiser & Stapler

[57] ABSTRACT

Individual manual device for the manipulation and the withdrawal of used needles for injection or for taking samples, which device makes it possible to avoid all contact between the needles and the user and is of the type comprising at least one jaw holding the needle during its withdrawal, wherein the device essentially comprises:
- a handle (1) for gripping by the user,
- a conical endpiece (3) for receiving the needle and comprising a fixed jaw,
- a movable jaw controlled by the user and depositing the needle by cooperating with the fixed jaw.

10 Claims, 2 Drawing Sheets

DEVICE FOR THE WITHDRAWAL OF NEEDLES

The present invention relates to an individual manual device for the manipulation and the withdrawal of used needles for injection or for taking samples, which device makes it possible to avoid all contact between the needles and the user and is of the type comprising at least one jaw holding the needle during its withdrawal.

The problem to be resolved consists in avoiding the risks of injury by pricking or by contact with used needles, in particular for avoiding the transmission of diseases such as AIDS or other viral or infectious diseases.

To this end, it is essential to store the used needles in receptacles which cannot be perforated, in order to avoid accidents during transportation of the discarded material.

Since the majority of injuries occur when replacing the cap of the needle or when disconnecting the needle by hand, it is therefore essential to eliminate all contact between the user's hands and the needle.

There are already devices available allowing such a result to be obtained.

Thus, U.S. Pat. No. 4,738,362 describes a system of receptacles made of plastic material and having one or more openings into which the needles are stuck.

After disconnecting the syringe, the needle falls into the container. The containers are destroyed after filling.

This device is very bulky and its handling is not very practical.

In a second group of devices described in PCT Applications WO 88/08313 and WO 88/06133, oblong tubes are proposed into which is introduced the needle to be withdrawn, which is extracted by being held by a retractable jaw integral with said tube.

These devices have the disadvantage of being of a geometrical shape of small width.

There is therefore some risk that the user, who must hold the body of the tube with one hand, will see the syringe slide over the top part of the tube and thereby injure the hand which is holding the latter.

The aim of the present invention is to overcome these disadvantages and to propose a device which is completely safe and of a simple design and whose function is straightforward and easily understood by the user.

According to the invention, this result is achieved with an individual manual device for the manipulation and the withdrawal of used needles for injection or for taking samples, which device makes it possible to avoid all contact between the needles and the user, and is of the type comprising at least one jaw holding the needle during its withdrawal, wherein the device essentially comprises:

- a handle for gripping by the user,
- a conical endpiece for receiving the needle and comprising a fixed jaw,
- a movable jaw controlled by the user and clamping the needle by cooperating with the fixed jaw.

The invention will be better understood from the following description of two embodiments given by way of non-limiting examples, with reference to the attached drawings in which.

Figure 1:
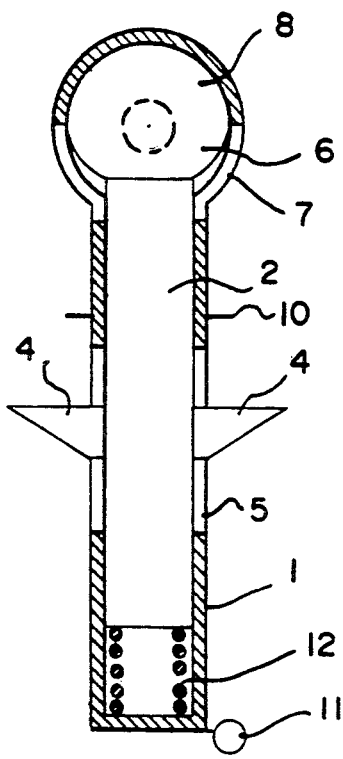
FIG. 1 is a plan view of a device according to the invention in a first embodiment, in a longitudinal section along A—A.
Figure 2:
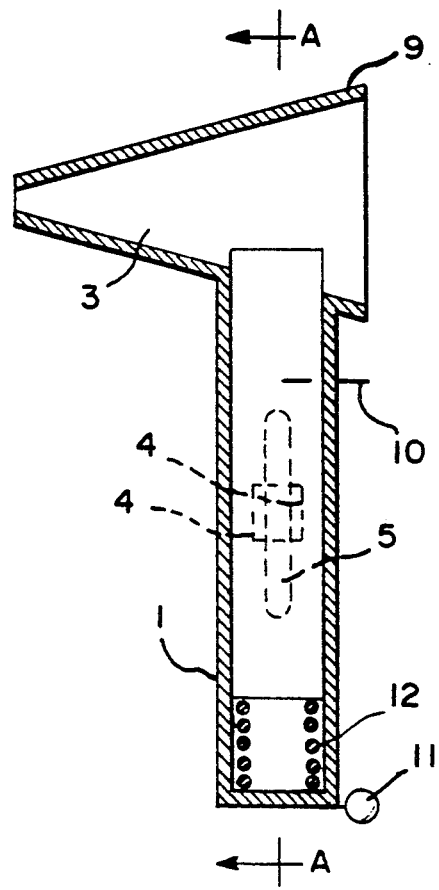
FIG. 2 is a cutaway side elevation view of the device in FIG. 1.
Figure 3:
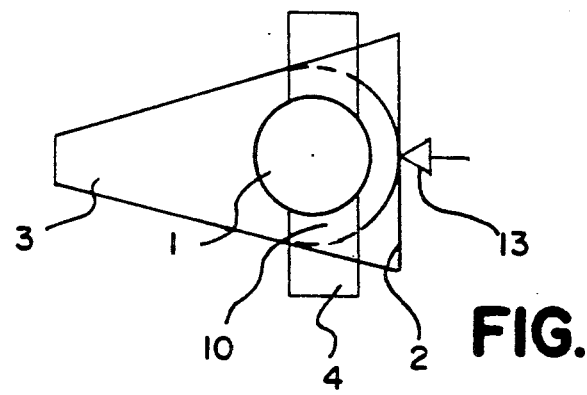
FIG. 3 is a rear view of the device in FIG. 1.

With reference to FIGS. 1, 2 and 3, the device comprises a handle (1) extended at the front by way of a truncated cone (3) placed at right angles to the handle (1).

Two movable levers (4) forming grips situated on either side of the handle (1) compress a spring (12) placed at the back inside the handle by driving a notched movable plate (6), or jaw, integral with a cylindrical sliding body (2) freeing an opening (15) at the center of the large base of the truncated cone (3) and permitting the introduction of the used needle (13) into the truncated cone. This movable plate (6) slides inside a groove (7) situated on the large base of the truncated cone (3). The levers (4) slide in slots (5) in the handle (1).

When the spring (12) is released, it pushes the movable plate (6) back against another fixed notched plate (8), or jaw, thereby immobilizing the needle between the two jaws.

A protective casing (9) situated on the large base of the truncated cone (3) and overlapping the rear of the movable plate (6) covers the space necessary for the movement of the latter. A casing (10) covers the front of the handle (1), separating it from the truncated cone (3).

The handle (1) advantageously comprises a means for hanging, such as a ring (11).

Figure 4:
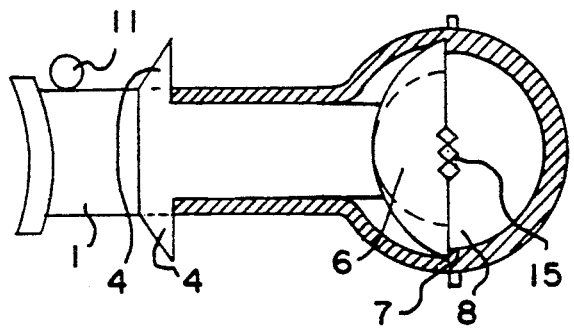
FIG. 4 is a plan view of an alternative embodiment.

In the variant of the device according to the invention as shown in FIG. 4, resting the index finger and the middle finger on the levers (4) and the thumb at the rear of the handle (1) creates an opening by means of retraction of the movable notched plate (6).

The spring (12) is circular and surrounds the fixed plate by passing through the groove (7) and the movable plate (6) by passing through the levers (4).

The functioning is as follows.

The two levers situated on either side of the middle of the handle of the apparatus are pulled backwards along slots (5) provided for this purpose in the handle.

As they are pulled back towards the rear of the apparatus, they pull back the cylindrical body (2) whose one end supports the notched movable plate (6) at its center, thereby freeing a space permitting the introduction of the tapered end of the needle at the center of the large base of the truncated cone.

The spring (12) is thus compressed.

By releasing the levers, said spring relaxes and pushes forward the cylindrical body at whose end the notched movable plate is fixed at its center.

The needle is thus blocked by this movable plate against an identical but fixed plate on the large base of the truncated cone.

The needle is thus situated in the truncated cone, the latter covering it completely, and it then suffices to disconnect the needle from its support A protective casing covers the front third of the large base of the truncated cone, thereby suppressing the opening necessary for the movement of said plate towards the rear. The conical shape of the receptacle for the needle permits recentering of the needle.

By presenting the small base of the truncated cone containing the needle above a recovery receptacle, and by once more actuating the levers towards the rear, the needle is released and falls by itself into the receptacle.

This device can be made of stainless steel or of plastic and for this reason can be sterilized hot or cold, depending on the case.

Figure 5:
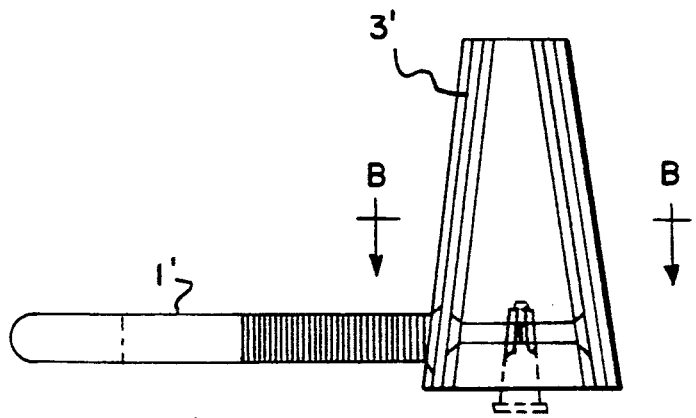
FIG. 5 is a side elevation view of an alternative embodiment of the device according to the invention.
Figure 6:
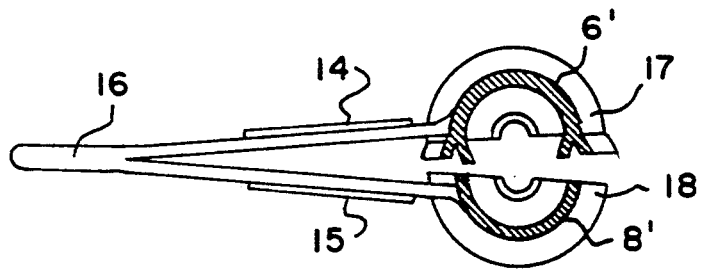
FIG. 6 is a plan view of the device in FIG. 5 in a partial cutaway along B—B.

The variant in FIGS. 5 and 6 again has the handle (1'), the cone (3') and two jaws (6', 8').

In this variant, the elastic return is provided by the handle (1') in two parts (14, 15) articulated at their end (16).

The functioning is thus identical to the above embodiment, the cone being made in two pieces (17, 18) which fit together.

I claim:

1. A discrete, manually operable device for manipulating and withdrawing a needle for injection or for taking samples, while avoiding all contact between the needle and a user of the device, comprising:
   a handle for gripping by the user;
   a conical endpiece extending from the handle and defining a protected receptacle for receiving the needle so that said contact between the needle and the user of the device is avoided, wherein the conical endpiece defines a central axis which is perpendicular to a central axis defined by the handle;
   a first jaw fixed to the conical endpiece;
   a movable member fixed for movement by the user relative to the handle; and
   a second jaw fixed to the movable member, for engaging the needle and for depositing the needle into the receptacle, in cooperation with the first jaw.

2. The device of claim 1 wherein the conical endpiece defines a diverging receptacle having a widened opening for receiving the needle.

3. The device of claim 2 wherein the widened opening is variable in size responsive to relative movements of the first jaw and the second jaw.

4. The device of claim 1 wherein the second jaw is normally biased into contact with the first jaw, so that the needle is normally engaged by the device.

5. The device of claim 4 wherein movement of the movable member relative to the handle operates to open the jaws to receive a needle to be manipulated, or to release a needle which has been manipulated.

6. A discrete, manually operable device for manipulating and withdrawing a needle for injection or for taking samples, while avoiding all contact between the needle and a user of the device, comprising:
   a handle for gripping by the user;
   a conical endpiece extending from the handle and defining a protected receptacle for receiving the needle so that said contact between the needle and the user of the device is avoided;
   a first jaw fixed to the conical endpiece;
   a movable member fixed for movement by the user relative to the handle;
   a second jaw fixed to the movable member, for engaging the needle and for depositing the needle into the receptacle, in cooperation with the first jaw;
   a pair of engagable levers forming grips extending from the movable member on opposing sides of the handle; and
   a spring located between the handle and the movable member, for biasing a notched movable plate forming the second jaw and integral with the moving member into contact with the first jaw;
   wherein gripping of the pair of engagable levers retracts the notched movable plate from the first jaw to expose an opening in base portions of the conical endpiece, and permits introduction of the needle into the receptacle.

7. The device of claim 6 wherein the notched movable plate is slidingly received in a groove formed in the base portions of the conical endpiece, and the engagable levers are slidingly received in slots formed in the handle.

8. The device of claim 7 wherein release of the pair of engagable levers urges the notched movable plate into contact with a fixed notched plate forming the first jaw, for immobilizing the needle between the fixed notched plate and the notched movable plate.

9. The device of claim 6 wherein the movable member is telescopingly received within the handle.

10. A discrete, manually operable device for manipulating and withdrawing a needle for injection or for taking samples, while avoiding all contact between the needle and a user of the device, comprising:
    a handle for gripping by the user;
    a conical endpiece extending from the handle and defining a protected receptacle for receiving the needle so that said contact between the needle and the user of the device is avoided;
    a first jaw fixed to the conical endpiece;
    a movable member fixed for movement by the user relative to the handle;
    a second jaw fixed to the movable member, for engaging the needle and for depositing the needle into the receptacle, in cooperation with the first jaw; and
    a split conical endpiece, one portion of which extends from the handle and another portion of which extends from the movable member;
    wherein the first jaw is fixed to the portion of the split conical endpiece which extends from the handle, and the second jaw is fixed to the portion of the split conical endpiece which extends from the movable member; and
    wherein distal ends of the handle and the movable member are attached to each other to provide an elastic return for movements of the movable member relative to the handle.

* * * * *